US011469001B2

(12) United States Patent
Takeda

(10) Patent No.: US 11,469,001 B2
(45) Date of Patent: Oct. 11, 2022

(54) MEDICAL INFORMATION PROCESSING SYSTEM AND MEDICAL INFORMATION PROCESSING METHOD

(71) Applicant: TOPCON CORPORATION, Tokyo (JP)

(72) Inventor: Noriyasu Takeda, Oakland, NJ (US)

(73) Assignee: TOPCON CORPORATION, Tokyo (JP)

( * ) Notice: Subject to any disclaimer, the term of this patent is extended or adjusted under 35 U.S.C. 154(b) by 206 days.

(21) Appl. No.: 15/921,838

(22) Filed: Mar. 15, 2018

(65) Prior Publication Data

US 2019/0287686 A1    Sep. 19, 2019

(51) Int. Cl.
*G16H 80/00* (2018.01)
*G06F 21/62* (2013.01)
*G16H 10/60* (2018.01)

(52) U.S. Cl.
CPC ......... *G16H 80/00* (2018.01); *G06F 21/6254* (2013.01); *G16H 10/60* (2018.01)

(58) Field of Classification Search
CPC ... G06F 19/325; G06F 21/6254; G16H 80/00; G16H 10/60; G16H 30/20; G16H 50/70; G16H 40/63
USPC .......................................................... 705/3
See application file for complete search history.

(56) References Cited

U.S. PATENT DOCUMENTS

| 6,397,224 | B1* | 5/2002 | Zubeldia | G06F 21/6254 |
| 2006/0036468 | A1* | 2/2006 | Thomas | G06Q 10/10 |
| | | | | 705/1.1 |
| 2006/0078171 | A1* | 4/2006 | Govindaraju | G06V 40/10 |
| | | | | 382/115 |

(Continued)

FOREIGN PATENT DOCUMENTS

JP    2001-318992 A    11/2001
JP    2002-312361 A    10/2002

(Continued)

OTHER PUBLICATIONS

Soloman I. Appavu; Analysis of Unique Patient Identifier Options; The Department of Health and Human Services; Nov. 24, 1997 (Year: 1997).*

(Continued)

*Primary Examiner* — Hiepv Nguyen
(74) *Attorney, Agent, or Firm* — Chiesa Shahinian & Giantomasi PC

(57) ABSTRACT

A system that includes a clinical database that stores clinical data in association with an internal identifier of a patient. An identifier conversion processor converts internal identifier associated with clinical data to an external identifier. An anonymization processor anonymizes confidential data in clinical data. An anonymized database stores anonymized data including anonymized clinical data and an external identifier associated with the anonymized clinical data. A research database stores anonymized data provided from the anonymized database for individual research projects. A research data provision processor receives a request from a (Continued)

user, reads out from the research database at least part of anonymized data associated with a research project to which the user belongs, and provides it to the user.

25 Claims, 6 Drawing Sheets

(56) References Cited

U.S. PATENT DOCUMENTS

| | | | |
|---|---|---|---|
| 2009/0049200 A1* | 2/2009 | Lin | G06F 16/258 709/246 |
| 2010/0034376 A1* | 2/2010 | Okuizumi | G06F 21/6254 380/44 |
| 2013/0151276 A1* | 6/2013 | Thiers | G06Q 50/22 705/2 |
| 2013/0346101 A1* | 12/2013 | Kahn | G06F 19/325 705/2 |

FOREIGN PATENT DOCUMENTS

| | | | |
|---|---|---|---|
| JP | 2007-140647 A | 6/2007 | |
| JP | 2010-267041 A | 11/2010 | |
| JP | 2013-109577 A | 6/2013 | |
| WO | WO-2014152305 A1 * | 9/2014 | G16H 50/20 |
| WO | 2016/185887 A1 | 11/2016 | |
| WO | WO-2018005562 A1 * | 1/2018 | G06F 21/6254 |

OTHER PUBLICATIONS

Notification of Reasons for Refusal dated May 10, 2022, in connection with Japanese Patent Application No. 2018-127390, 6 pgs (including translation).

* cited by examiner

MEDICAL INFORMATION PROCESSING SYSTEM AND MEDICAL INFORMATION PROCESSING METHOD

FIELD

Embodiments relate to a system and a method for processing medical information.

BACKGROUND

A variety of information is handled in health facilities. Typical examples thereof include examination order information showing the contents of examination orders, examination data showing the contents and/or the results of examinations, diagnostic data showing the contents and/or the results of diagnoses, surgical data showing the contents and/or the results of surgeries, medication data showing the types and/or the amounts of medicine administered, and health care fee information showing at least one of the contents, the points and the amounts of health care fees. Such medical information is managed using systems such as an electronic medical record system, an image management system, an ordering system, a medical accounting system. These systems are called a hospital information system (HIS).

Clinically acquired data such as examination data, diagnostic data, surgical data and medication data is called clinical data. Conventionally, clinical data has generally been handled only within the facility in which the clinical data was acquired. In recent years, however, there is also a movement to share clinical data among a plurality of facilities (see International Publication WO2016/185887, for example).

Information security measures are extremely important in inter-facility systems sharing information between facilities, in order to prevent specification of individual patient and leakage of personal information. The security of medical information is legislated in each country.

Meanwhile, application of computing technologies such as artificial intelligence and statistical computing to the medical field has been advanced. For that purpose, building a large scale database of clinical data (for example, making big data including clinical data) is required.

However, in the present situation, data collection and anonymization are substantially done manually. This leads to problems such as increased labor and efforts, occurrence of human errors, loss of time and expense, and deterioration of quality. Therefore, a database of clinical data that can be effectively accessed from a plurality of facilities has not yet been realized.

DETAILED DESCRIPTION

Figure 1:
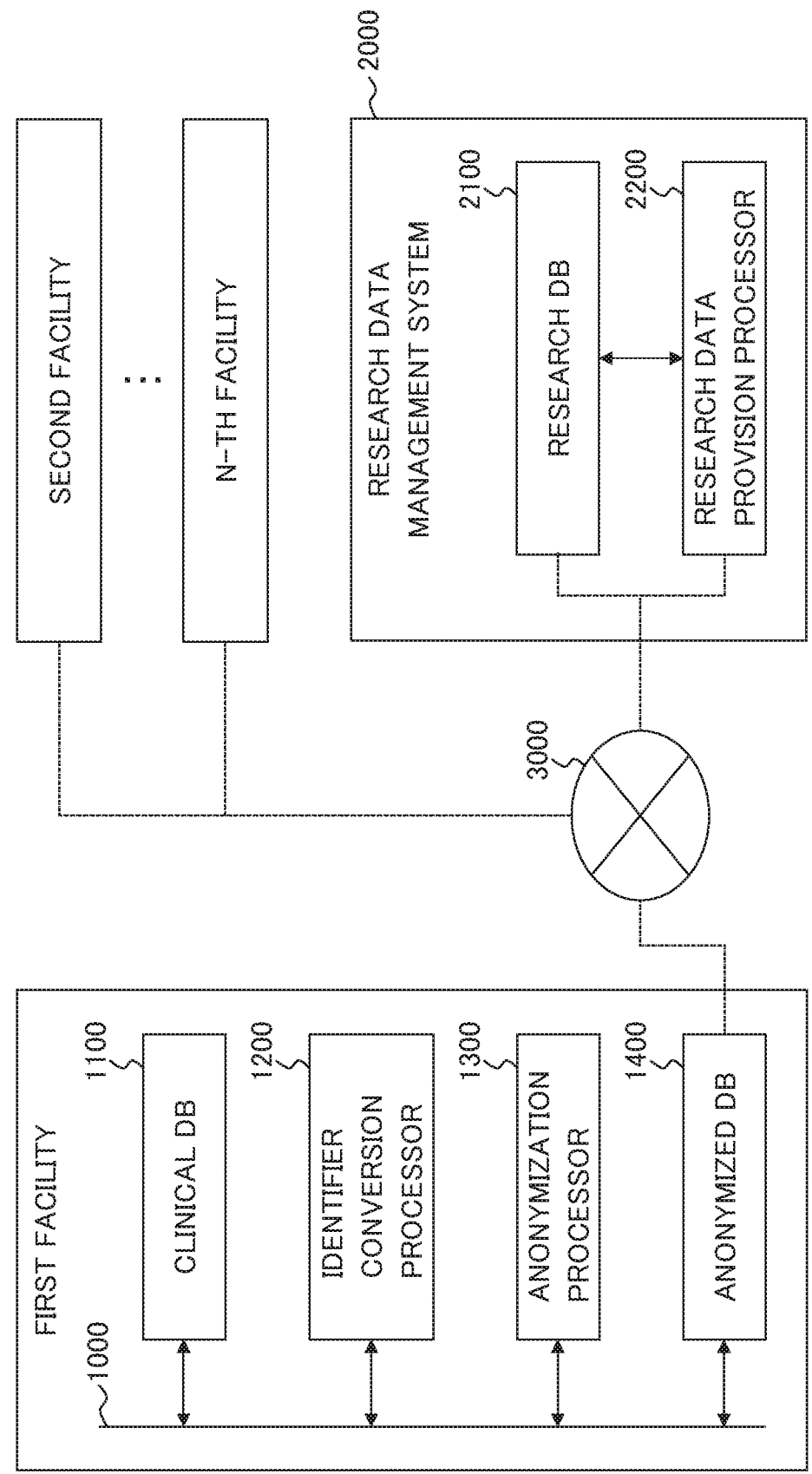
FIG. 1 is a schematic diagram illustrating an example of the configuration of the medical information processing system according to an exemplary embodiment.

A purpose of an exemplary embodiment is to realize a database of clinical data that can be effectively utilized from a plurality of facilities while securing security.

The first aspect of the exemplary embodiment is a medical information processing system including: a plurality of clinical databases respectively associated with a plurality of health facilities, wherein each of the plurality of clinical databases stores clinical data acquired in a corresponding health facility in association with an internal identifier assigned to a patient; a plurality of identifier conversion processors respectively associated with the plurality of health facilities, wherein each of the plurality of identifier conversion processors converts an internal identifier associated with clinical data stored in a clinical database of a corresponding health facility to an external identifier; a plurality of anonymization processors respectively associated with the plurality of health facilities, wherein each of the plurality of anonymization processors acquires clinical data from a clinical database of a corresponding health facility and anonymizes predetermined confidential data included in the clinical data acquired; a plurality of anonymized databases respectively associated with the plurality of health facilities, wherein each of the plurality of anonymized databases stores anonymized data including clinical data anonymized by an anonymization processor of a corresponding health facility and an external identifier associated with the anonymized clinical data by an identifier conversion processor of the corresponding health facility; and a research data management system installed in a facility other than any of the plurality of health facilities, wherein the research data management system includes: a research database that stores anonymized data provided from the plurality of anonymized databases for individual research projects set in advance; and a research data provision processor that receives a request from a user, reads out from the research database at least part of anonymized data associated with a research project to which the user belongs, and provides it to the user.

The second aspect of the exemplary embodiment is a medical information processing system capable of performing data communication with a clinical database that stores clinical data acquired in a health facility in association with an internal identifier assigned to a patient, the medical information processing system including: a plurality of identifier conversion processors respectively associated with a plurality of health facilities, wherein each of the plurality of identifier conversion processors converts an internal identifier associated with clinical data stored in a clinical database of a corresponding health facility to an external identifier; a plurality of anonymization processors respectively associated with the plurality of health facilities, wherein each of the plurality of anonymization processors acquires clinical data from a clinical database of a corresponding health facility and anonymizes predetermined confidential data included in the clinical data acquired; a plurality of anonymized databases respectively associated with the plurality of health facilities, wherein each of the plurality of anonymized databases stores anonymized data including clinical data anonymized by an anonymization processor of a corresponding health facility and an external identifier associated with the anonymized clinical data by an identifier conversion processor of the corresponding health facility; and a research data management system installed in a facility other than any of the plurality of health facilities, wherein the research data management system includes: a research database that stores anonymized data provided from the plurality of anonymized databases for individual research projects set in advance; and a research data provision processor that receives a request from a user, reads out from the research database at least part of anonymized data associated with a research project to which the user belongs, and provides it to the user.

The third aspect of the exemplary embodiment is the medical information processing system of the first aspect, wherein the research data management system further includes a research data deletion processor that receives a data deletion request including an external identifier from one of the plurality of health facilities and deletes anonymized data including the external identifier included in the data deletion request from the research database.

The fourth aspect of the exemplary embodiment is the medical information processing system of the second aspect, wherein the research data management system further includes a research data deletion processor that receives a data deletion request including an external identifier from one of the plurality of health facilities and deletes anonymized data including the external identifier included in the data deletion request from the research database.

The fifth aspect of the exemplary embodiment is the medical information processing system of the first aspect, wherein the anonymized data includes numerical data extracted from clinical data that has been anonymized by the anonymization processor and an external identifier that has been associated with the clinical data by the identifier conversion processor.

The sixth aspect of the exemplary embodiment is the medical information processing system of the second aspect, wherein the anonymized data includes numerical data extracted from clinical data that has been anonymized by the anonymization processor and an external identifier that has been associated with the clinical data by the identifier conversion processor.

The seventh aspect of the exemplary embodiment is the medical information processing system of the first aspect, wherein the anonymized data includes image data extracted from clinical data that has been anonymized by the anonymization processor and an external identifier that has been associated with the clinical data by the identifier conversion processor.

The eighth aspect of the exemplary embodiment is the medical information processing system of the second aspect, wherein the anonymized data includes image data extracted from clinical data that has been anonymized by the anonymization processor and an external identifier that has been associated with the clinical data by the identifier conversion processor.

The ninth aspect of the exemplary embodiment is the medical information processing system of the first aspect, wherein at least one of the plurality of identifier conversion processors each is configured to assign a same external identifier to a same internal identifier, the anonymized data includes acquisition date information that shows a date on which corresponding clinical data has been acquired, and the research database stores two or more pieces of anonymized data corresponding to a same external identifier according to a time-dependent order based on two or more pieces of acquisition date information included in the two or more pieces of anonymized data.

The tenth aspect of the exemplary embodiment is the medical information processing system of the second aspect, wherein at least one of the plurality of identifier conversion processors each is configured to assign a same external identifier to a same internal identifier, the anonymized data includes acquisition date information that shows a date on which corresponding clinical data has been acquired, and the research database stores two or more pieces of anonymized data corresponding to a same external identifier according to a time-dependent order based on two or more pieces of acquisition date information included in the two or more pieces of anonymized data.

The eleventh aspect of the exemplary embodiment is the medical information processing system of the first aspect, wherein in a case where two or more different internal identifiers have been assigned to a same patient and the two or more internal identifiers are associated with each other, the identifier conversion processor assigns a same external identifier to the two or more internal identifiers, the anonymized data includes acquisition date information that shows a date on which corresponding clinical data has been acquired, and the research database stores two or more pieces of anonymized data corresponding to a same external identifier according to a time-dependent order based on two or more pieces of acquisition date information included in the two or more pieces of anonymized data.

The twelfth aspect of the exemplary embodiment is the medical information processing system of the second aspect, wherein in a case where two or more different internal identifiers have been assigned to a same patient and the two or more internal identifiers are associated with each other, the identifier conversion processor assigns a same external identifier to the two or more internal identifiers, the anonymized data includes acquisition date information that shows a date on which corresponding clinical data has been acquired, and the research database stores two or more pieces of anonymized data corresponding to a same external identifier according to a time-dependent order based on two or more pieces of acquisition date information included in the two or more pieces of anonymized data.

The thirteenth aspect of the exemplary embodiment is the medical information processing system of the eleventh aspect, wherein in a case where at least one of the plurality of health facilities each includes two or more medical locations, the two or more internal identifiers respectively correspond to the two or more medical locations.

The fourteenth aspect of the exemplary embodiment is the medical information processing system of the twelfth aspect, wherein in a case where at least one of the plurality of health facilities each includes two or more medical locations, the two or more internal identifiers respectively correspond to the two or more medical locations.

The fifteenth aspect of the exemplary embodiment is the medical information processing system of the first aspect, wherein in a case where at least one of the plurality of health facilities each includes two or more medical locations, a same internal identifier is assigned to a same patient in the two or more medical locations.

The sixteenth aspect of the exemplary embodiment is the medical information processing system of the second aspect, wherein in a case where at least one of the plurality of health facilities each includes two or more medical locations, a same internal identifier is assigned to a same patient in the two or more medical locations.

The seventeenth aspect of the exemplary embodiment is the medical information processing system of the first aspect, wherein the research data provision processor receives a request from a user, reads out at least part of anonymized data associated with a research project to which the user belongs from the research database, converts a file format of the read-out anonymized data to a file format associated in advance with the user or with the research project, and provides the converted anonymized data to the user.

The eighteenth aspect of the exemplary embodiment is the medical information processing system of the second aspect, wherein the research data provision processor receives a request from a user, reads out at least part of anonymized data associated with a research project to which the user belongs from the research database, converts a file format of the read-out anonymized data to a file format associated in advance with the user or with the research project, and provides the converted anonymized data to the user.

The nineteenth aspect of the exemplary embodiment is the medical information processing system of the first aspect, wherein the research data management system further includes an analysis database that receives analysis data generated from an analysis performed by a user based on anonymized data provided to the user and stores the analysis data.

The twentieth aspect of the exemplary embodiment is the medical information processing system of the second aspect, wherein the research data management system further includes an analysis database that receives analysis data generated from an analysis performed by a user based on anonymized data provided to the user and stores the analysis data.

The twenty-first aspect of the exemplary embodiment is the medical information processing system of the first aspect, wherein at least one of the plurality of anonymization processors each includes a confidential item setting processor that sets an item of the predetermined confidential data.

The twenty-second aspect of the exemplary embodiment is the medical information processing system of the second aspect, wherein at least one of the plurality of anonymization processors each includes a confidential item setting processor that sets an item of the predetermined confidential data.

The twenty-third aspect of the exemplary embodiment is the medical information processing system of the twenty-first aspect, wherein the confidential item setting processor sets the item according to a region in which a corresponding health facility exists.

The twenty-fourth aspect of the exemplary embodiment is the medical information processing system of the twenty-second aspect, wherein the confidential item setting processor sets the item according to a region in which a corresponding health facility exists.

The twenty-fifth aspect of the exemplary embodiment is the medical information processing system of the twenty-third aspect, further including a region determiner that determines a region in which the corresponding health facility exists, wherein the confidential item setting processor sets the item based on an output from the region determiner.

The twenty-sixth aspect of the exemplary embodiment is the medical information processing system of the twenty-fourth aspect, further including a region determiner that determines a region in which the corresponding health facility exists, wherein the confidential item setting processor sets the item based on an output from the region determiner.

The twenty-seventh aspect of the exemplary embodiment is a method of processing medical information, the method including: storing, in corresponding one of a plurality of clinical databases respectively associated with a plurality of health facilities, clinical data acquired in a corresponding health facility in association with an internal identifier assigned to a patient; converting an internal identifier associated with clinical data stored in a clinical database of a corresponding health facility to an external identifier, by corresponding one of a plurality of identifier conversion processors respectively associated with the plurality of health facilities; acquiring clinical data from a clinical database of a corresponding health facility and anonymizing predetermined confidential data included in the acquired clinical data, by corresponding one of a plurality of anonymization processors respectively associated with the plurality of health facilities; storing, in corresponding one of a plurality of anonymized databases respectively associated with the plurality of health facilities, anonymized data including clinical data anonymized by an anonymization processor of a corresponding health facility and an external identifier associated with the anonymized clinical data by an identifier conversion processor of the corresponding health facility; storing anonymized data provided from the plurality of anonymized databases for individual research projects set in advance, in a research database installed in a facility other than any of the plurality of health facilities; and receives a request from a user, reading out from the research database at least part of anonymized data associated with a research project to which the user belongs, and providing it to the user, by a research data provision processor installed in a facility other than any of the plurality of health facilities.

It is possible to combine steps executable by the medical information processing system according to any of the third to twenty-sixth aspects, to the medical information processing method according to the twenty-seventh aspect.

Any of the elements included in the medical information processing system according to the exemplary embodiment described below can be combined with the medical information processing system according to any of the first to twenty-sixth aspects.

Any process executable by the medical information processing system according to the exemplary embodiment described below can be combined with the medical information processing method according to the twenty-seventh aspect.

Examples of the medical information processing system and the medical information processing method according to the exemplary embodiment will be described in detail with referring to the drawings. It is to be noted that the contents of the documents cited in this specification and any other known techniques can be incorporated in the exemplary embodiments.

A medical information processing system according to the exemplary embodiment is configured to process medical information acquired in a plurality of facilities. A single health facility may include only one facility (only one location, only one site), or a single health facility may include two or more facilities (two or more locations, two or more sites). In other words, the plurality of facilities to which the medical information processing system can be applied include one or both of one or more health facilities each consisting of only a single facility and one or more health facilities each consisting of two or more facilities.

The medical information processing system includes one or more information processing systems installed in each of the plurality of facilities and one or more information systems installed in a facility other than any of the plurality of facilities.

A hospital information system (HIS) is known as an example of the information system installed inside a facility. A network system that provides at least one of the functions of a hospital information system using cloud computing technology is known as an example of a hospital information system installed outside a facility. A hospital information system may include at least part of an information system constructed over two or more facilities or may include at least part of an information system including an information system in a facility and an information system outside the facility that are capable of operating together.

The hospital information system is generally an information system for processing information handled within a health facility (or within a facility). The information system included in the hospital information system may be a known information system. A typical hospital information system includes an ordering system, an electronic medical record system, an image management system, a medical accounting system, and the like. Two or more information systems included in the hospital information system are configured to operate in conjunction with each other.

The ordering system is a system for transmitting various kinds of order information such as examination orders, prescription orders, and medication orders. For example, the ordering system receives order information from an information terminal and transmits the order information to a relevant department (e.g., an examination department, a radiology department, a pharmaceutical department) in the facility via a network. An examination may be sampling, physiological examination, or radiography. These examinations are generally carried out in a department other than the department to which the doctor who issued the order belongs. On the other hand, examinations may be carried out within the same department as the doctor belongs. For example, in ophthalmology, it is common to perform observation, imaging and measurement of the patient's eye within the ophthalmology department. The ordering system includes, for example, a processor (e.g., a computer, a server) for executing processing order information etc., a storage device (e.g., a database) for storing order information etc., and a communication device conforming to a communication standard.

The electronic medical record system is an information system (e.g., a filing system) for storing and managing electronic medical records created for individual patients. The electronic medical records are data obtained by digitizing and recording information in medical records. The electronic medical record of each patient is identified and managed with a patient ID (an internal identifier) used within a concerned facility. The electronic medical record system receives and stores an electronic medical record created by a computer such as a doctor terminal. The electronic medical record system receives a request from a computer such as a doctor terminal and provides information recorded in an electronic medical record to the computer via the network. The electronic medical record system receives an electronic medical record edited using a computer such as a doctor terminal and updates the contents of the electronic medical record of the patient. The electronic medical record system may include at least part of a system(s) utilized within a single facility or may include at least part of a system(s) mutually utilized among a plurality of facilities. The electronic medical record system includes, for example, a processor (e.g., a computer, a server) for performing processing of electronic medical record information etc., a storage device (e.g., a database) for storing electronic medical record information etc., and a communication device conforming to the communication standard.

The image management system is an information system for storing and managing medical images of individual patients. A medical image of each patient is identified and managed with a patient ID (an internal identifier) used within a concerned facility. A typical example of an image management system is a picture archiving and communication system (PACS). The PACS receives medical images such as X-ray photograph images, X-ray CT images, MRI images and the like from modality devices and stores and manages the medical images. In addition, an image management system specialized for a specific department is also widely used. For example, in the ophthalmology department, an examination room (an imaging room) is provided in which modality devices such as a fundus camera (retinal camera), a slit lamp microscope, an optical coherence tomography (OCT) apparatus, and a scanning laser ophthalmoscope (SLO) are installed. Medical images relating to all departments are integrated and linked according to a standard called digital imaging and communications in medicine (DICOM). The image management system receives a request from a computer such as a doctor terminal, a viewer, or an analysis device, and provides a medical image to the computer via a network. When diagnosis, analysis or interpretation is performed using the medical image, the result thereof is transmitted to the image management system and/or the electronic medical record system to be stored and managed. The image management system includes, for example, a processor (e.g., a computer, a server) for performing processing relating to medical images etc., a storage device (e.g., a database) for storing medical images etc., and a communication device conforming to the communication standard.

The medical accounting system prepares a health care fee statement based on information stored and managed by the hospital information system. Furthermore, the medical accounting system may have a function for inputting medical treatment contents, a function for calculating the amount to be paid at the reception counter (payment amount for a patient), a function for issuing a prescription, a function for managing a medication fee, a function for issuing medicine information, a function for issuing a receipt, and the like. The medical accounting system includes, for example, a processor (e.g., a computer, a server) for performing processing of accounting related information etc., a storage device (e.g., a database) for storing accounting related information etc., and a communication device conforming to the communication standard.

The hospital information system according to the exemplary embodiment, which may include a cloud computing system, has a clinical data management function including at least the electronic medical record management function and the image management function described above. Also, the hospital information system according to the exemplary embodiment may include other functions relating to medical information processing. Examples of such functions include a surgery management function, a rehabilitation management function, a hospitalization management function, a nutrition management function, a comprehensive hospital-ward management function, a comprehensive outpatient management function, a comprehensive department management function, a pathology management function, an examination management function, a clinical examination management function, a radiology department management function (radiology information system, or RIS), a diagnostic imaging management function, a dialysis management function, a regional medical networking function, a patient information management function, a work improvement management function, an article management function, and a personnel management function.

The hospital information system according to the exemplary embodiment may include any of the followings: a portable computer such as a tablet terminal or smartphone; an output device such as a display device or a printing device; and an input device such as an operation device or a reading device.

Various kinds of medical apparatuses for acquiring clinical data are installed in the facility. Typically, an examination apparatus (a measurement apparatus) for acquiring examination data (e.g., numerical data, a characteristic map), an imaging apparatus for acquiring image data, etc. are installed in the facility.

For example, in ophthalmology, various kinds of ophthalmologic measurement apparatuses and various kinds of ophthalmologic imaging apparatuses are utilized. Examples of ophthalmologic measurement apparatuses include an ophthalmologic examination apparatus (e.g., an optotype presenting apparatus, a phoropter), an eye refraction examination apparatus (e.g., a refractometer, a keratometer), a tonometer, a specular microscope, a wave front analyzer, a perimeter, and a microperimeter. An ophthalmologic measurement apparatus may include an application software for analyzing measurement data. Examples of ophthalmologic imaging apparatuses include a slit lamp microscope, a fundus camera, an SLO, and an OCT. An ophthalmologic imaging apparatus may include an application software for analyzing images acquired.

Departments other than ophthalmology utilize, for example, an ultrasound diagnostic apparatus, an X-ray imaging apparatus, an X-ray CT apparatus, an MRI apparatus, an endoscope system, an automatic analyzer (e.g., a biopsy apparatus), and a gene analyzer.

In the exemplary embodiment, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), a combination of two or more circuits, or an apparatus/device or a system that includes two or more circuits. The processor can realize the functions according to the present embodiment, for example, by reading out and executing a program or data stored in a storage circuit or a storage device.

Hereinafter, a plurality of exemplary embodiments will be described. Any two or more of these embodiments can be combined. In addition, any known technique can be combined with any one or a combination of any two or more of the plurality of exemplary embodiments.

First Embodiment

A medical information processing system according to an exemplary first embodiment will be described. FIG. 1 shows an example of the configuration of the medical information processing system according to the present embodiment.

The medical information processing system illustrated in FIG. 1 includes information processing systems installed in the first to the N-th facilities, and the research data management system 2000 installed in a facility other than any of these N facilities. The information processing systems provided in the first to the N-th facilities each can communicate with the research data management system 2000 via the communication path (communication line) 3000.

Each of the first to the N-th facilities is a medical location. Similar information processing systems are installed in the facilities (n-th facility: n=1, 2, . . . , N, where N is an integer equal to or larger than 2). For example, as shown in FIG. 1, the first facility includes the clinical database (clinical DB) 1100, the identifier conversion processor 1200, the anonymization processor 1300, and the anonymized database (anonymized DB) 1400. It should be noted that the clinical database 1100 may be included in the medical information processing system or may not be included therein.

The clinical database 1100, the identifier conversion processor 1200, the anonymization processor 1300, and the anonymized database 1400 are connected to each other via a communication path built within the first facility (i.e., an intra-hospital network such as a local area network).

Although not shown in the figures, the above-described various kinds of examination apparatuses, measurement apparatuses, and imaging apparatuses are installed in each facility.

<Clinical Database 1100>

The clinical database 1100 installed in the first facility is associated with the first facility (or, with the health facility to which the first facility belongs). For example, at least part of the clinical database 1100 is installed inside the first facility and/or at least part of the clinical database 1100 is installed outside the first facility. A database utilizing a cloud computing system is an example of the clinical database 1100 at least part of which is installed outside the first facility.

The clinical database 1100 installed in the first facility stores the clinical data acquired in the first facility (and further, in the health facility to which the first facility belongs) in association with the internal identifier assigned to a patient (e.g., the patient ID). The clinical database 1100 includes, for example, an electronic medical record system and an image management system. The creation and management of electronic medical records, the acquisition and management of images, and the like can be executed in the same manner as in the conventional ways.

Examples of the items of clinical data stored in the clinical database 1100 include internal identifiers (patient IDs), examination data, measurement data, image data, names, ages, genders, addresses, telephone numbers, social security numbers, health insurance numbers, dates, etc. Examples of examination data and measurement data in ophthalmology include objective refractive power values (S, C, A), subjective visual acuity values (VA), intraocular pressure values (IOP), ocular axial lengths (AL), corneal shapes (TOPO), visual fields (VF), electronic medical record (EMR) information of other kinds, OCT images, imaging conditions (imaging parameters), fundus photographs, infrared moving images, and images of other kinds.

<Identifier Conversion Processor 1200>

The identifier conversion processor 1200 installed in the first facility is associated with the first facility (or, with the health facility to which the first facility belongs). For example, at least part of the identifier conversion processor 1200 is installed inside the first facility and/or at least part thereof is installed outside the first facility. A processor utilizing a cloud computing system is an example of the identifier conversion processor 1200 at least part of which is installed outside the first facility.

The identifier conversion processor 1200 installed in the first facility converts the internal identifier associated with clinical data stored in the clinical database 1100 corresponding to the first facility (or the health facility to which the first facility belongs), to an external identifier.

Here, as described above, internal identifiers are identifiers (i.e., clinical patient IDs) assigned to individual patients for patient identification within the first facility (or the health facility to which the first facility belongs). On the other hand, external identifiers are identifiers used for patient identification outside the first facility, and are identifiers (i.e., research patient IDs) used for the purpose of research in the present embodiment. The identifier conversion processor 1200 is configured to convert a clinical patient ID (i.e., an internal identifier) used inside the first facility to a research patient ID (i.e., an external identifier) used outside the first facility.

The identifier conversion processor 1200 may be configured to retain an internal identifier and an external identifier in association with each other. For example, the identifier conversion processor 1200 can record an internal identifier and an external identifier obtained by converting the internal identifier in association with each other. A correspondence information such as a table can be used as an example of the association between internal identifiers and external identifiers.

The identifier conversion processor 1200 may be configured to convert an internal identifier to an external identifier in such a manner that the internal identifier cannot be reproduced from the external identifier.

<Anonymization Processor 1300>

The anonymization processor 1300 installed in the first facility is associated with the first facility (or the health facility to which the first facility belongs). For example, at least part of the anonymization processor 1300 is installed inside the first facility and/or at least part thereof is installed outside the first facility. A processor utilizing a cloud computing system is an example of the anonymization processor 1300 at least part of which is installed outside the first facility.

The anonymization processor 1300 installed in the first facility acquires clinical data from the clinical database 1100 corresponding to the first facility (or the health facility to which the first facility belongs), and anonymizes predetermined confidential data contained in the clinical data acquired.

The anonymization may include a data processing method of an arbitrary type. For example, the anonymization may include any one or more of the followings: deletion, addition, change, replacement (or substitution), conversion, generalization, encryption, randomization, machine learning, pseudonymization, noise addition, and rearrangement. Examples of anonymization methods include k-anonymization and Pk-anonymization.

Confidential data is data on a patient or the like about predetermined confidential items. Confidential data is not limited to data relating to a patient oneself, but may include data on household members, data on relatives, data on employers, or the like.

Confidential items are preset in typical cases. Confidential items may be set, for example, based on the laws applied to the region (e.g., a country, regional federation/coalition/union/association, etc.) where the medical information processing system is used. Examples of confidential items include the following (A) to (R).

(A) Names (B) All geographic subdivisions smaller than a State, including street address, city, county, precinct, zip code, and their equivalent geocodes, except for the initial three digits of a zip code if, according to the current publicly available data from the Bureau of the Census: (1) The geographic unit formed by combining all zip codes with the same three initial digits contains more than 20,000 people; and (2) The initial three digits of a zip code for all such geographic units containing 20,000 or fewer people is changed to "000"

(C) All elements of dates (except year) for dates directly related to an individual, including birth date, admission date, discharge date, date of death; and all ages over 89 and all elements of dates (including year) indicative of such age, except that such ages and elements may be aggregated into a single category of age 90 or older (D) Telephone numbers (E) Fax numbers (F) Electronic mail addresses (G) Social security numbers (H) Medical record numbers (I) Health plan beneficiary numbers (J) Account numbers (K) Certificate/license numbers (L) Vehicle identifiers and serial numbers, including the license plate numbers (M) Device identifiers and serial numbers (N) Web Universal Resource locators (URLs)

(O) Internet Protocol (IP) address numbers (P) Biometric identifiers, including finger and voice prints (Q) Full face photographic images and any comparable images (R) Any other unique identifying number, characteristic, or code, except as permitted by (C) above Depending on the region, the followings etc. are required in principle: collecting data in conformity with a specific purpose of use; not processing data contrary to the purpose of use; not retaining data longer than necessary in a form that can identify an individual; and applying an anonymization method incapable of re-identification. In such a region, as described above, it is desired that the identifier conversion processor 1200 is configured to execute the conversion from an internal identifier to an external identifier so that the internal identifier cannot be reproduced from the external identifier.

<Anonymized Database 1400>

The anonymized database 1400 installed in the first facility is associated with the first facility (or the health facility to which the first facility belongs). For example, at least part of the anonymized database 1400 is installed inside the first facility and/or at least part thereof is installed outside the first facility. A database utilizing a cloud computing system is an example of the anonymized database 1400 at least part of which is installed outside the first facility.

The anonymized database 1400 installed in the first facility stores anonymized data that includes clinical data anonymized by the anonymization processor 1300 corresponding to the first facility (or the health facility to which the first facility belongs) and an external identifier associated with the clinical data by the identifier conversion processor 1200.

For example, suppose that clinical data includes an internal identifier (i.e., a clinical patient ID), examination data, measurement data, image data, name, age, gender, address, telephone number, social security number, and date.

In this case, the identifier conversion processor 1200 converts the internal identifier (i.e., clinical patient ID) to an external identifier (i.e., a research patient ID).

Also, the anonymization processor 1300 deletes the name, the address, the telephone number, the social security number, and the date from the clinical data. As a result of this, the clinical data anonymized by the anonymization processor 1300 includes only the examination data, the measurement data, the image data, the age, and the gender.

As such, anonymized data stored in the anonymized database 1400 in the present example includes only an external identifier (i.e., research patient ID), examination data, measurement data, image data, age, and gender.

Incidentally, examination data and measurement data may include numerical data. A numerical value showing the degree of a predetermined matter (for example, a possibility of suffering from a predetermined disease) is an example of numerical data included in examination data. In addition, a measurement value of a predetermined parameter is an example of numerical data included in measurement data.

<Research Data Management System 2000>

The research data management system 2000 is installed in a facility other than any of the first to the N-th facilities. The research data management system 2000 receives anonymized data created at the first to the N-th facilities, and stores and manages the received anonymized data as data for research. The research data management system 2000 includes the research database 2100 and the research data provision processor 2200.

<Research Database 2100>

The research database 2100 stores anonymized data provided from a plurality of anonymized databases 1400 corresponding to the first to the N-th facilities for individual research projects that have been set in advance. It should be noted that anonymized data provided for research may be referred to as research data. For example, anonymized data registered in the research database 2100 may be referred to as research data.

The provision of anonymized data from the anonymized database 1400 to the research database 2100 is performed in an arbitrary manner. For example, the medical information processing system may be configured to send anonymized data from the anonymized database 1400 to the research database 2100 on a regular or irregular basis according to a preset schedule.

The medical information processing system may be configured to transmit anonymized data from the anonymized database 1400 to the research database 2100 in response to an instruction or a request from a user in the facility in which the anonymized database 1400 is installed. The transmission instruction of anonymized data is performed using a computer installed in the same facility as that of the anonymized database 1400, for example.

The medical information processing system may be configured to transmit anonymized data from the anonymized database 1400 to the research database 2100 in response to an instruction or a request from the research data management system 2000 or other systems (e.g., other apparatuses or devices).

The medical information processing system may be configured to be capable of selecting anonymized data to be sent to the research database 2100 from among anonymized data stored in the anonymized database 1400. Examples of the modes of selecting anonymized data include the followings: selection of a patient (e.g., selection of an internal identifier or an external identifier); selection of a patient attribute (e.g., selection of gender, age, etc.); selection of a disease; selection of a body part; selection of an examination; selection according to a result of an examination (e.g., selection of a patient whose examination result indicates the possibility of a disease); selection of a modality (an imaging apparatus); selection according to a result of image analysis (e.g., selection of a patient whose analysis result indicates the possibility of a disease). The selection of anonymized data is performed using a computer installed in the same facility as that of the anonymized database 1400, for example.

For example, the research data management system 2000 issues identifiers (i.e., research project IDs) for individual research projects that are set in advance. Assigning research project IDs to research data allows research data to be managed for individual research projects.

The medical information processing system may be configured so that a user in the facility in which the anonymized database 1400 is installed can designate a research project corresponding to anonymized data concerned. The designation of a research project is done, for example, by designating or entering a research project ID.

<Research Data Provision Processor 2200>

In response to a request from a user, the research data provision processor 2200 reads out, from the research database 2100, at least part of the research data associated with the research project to which the user belongs. In addition, the research data provision processor 2200 provides the read-out data to the user.

The user requesting the provision of research data is, for example, a researcher (e.g., a doctor) who belongs to any of the first to the N-th facilities, any of the first to the N-th facilities, or an apparatus/device (e.g., a computer) installed in any of the first to the N-th facilities. The user identification and authentication are performed using identifiers (i.e., research user IDs) assigned in advance to users such as researchers, facilities, apparatuses/devices, and the like, as well as passwords.

The research data provision processor 2200 may be configured to execute the following processes: receiving a request from a user; reading out at least part of the research data associated with the research project to which the user belongs, from the research database; converting the file format of the read-out research data into a file format associated in advance with the user or with the research project; and providing the converted research data to the user.

The file formats of research data to be provided are set in advance by users, for example. The file formats may be arbitrary and are typically set according to software respective users use for analyzing research data. Examples of the file formats of research data to be provided are CSV, XML, JSON, and the like.

Note that anonymized data created in file formats conformable to provision and anonymized data converted to file formats conformable to provision may be stored in the anonymized database 1400.

<Usage Mode>

Figure 2:
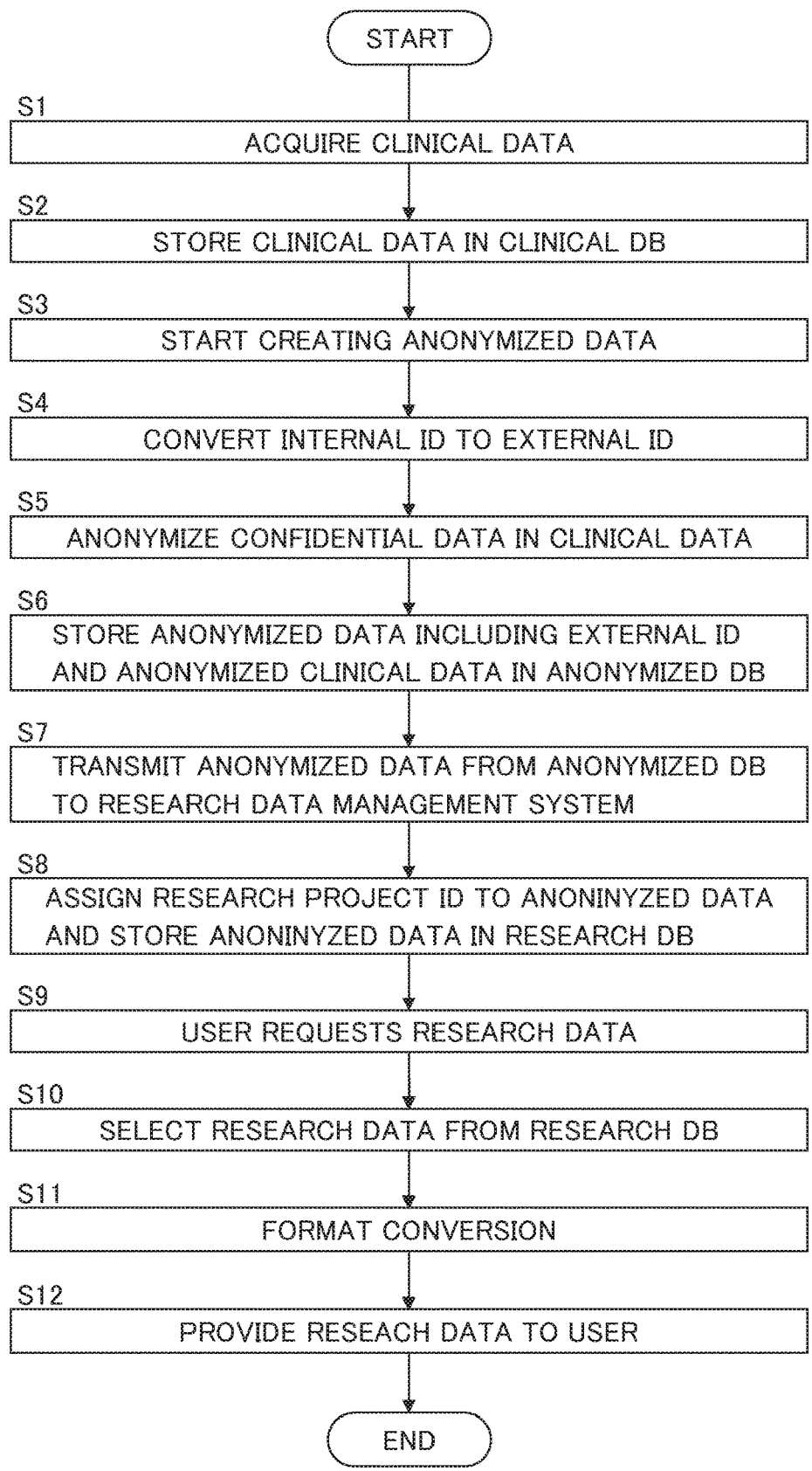
FIG. 2 is a flowchart illustrating an example of the usage mode of the medical information processing system according to the exemplary embodiment.

A usage mode of the medical information processing system according to the present embodiment will be described. An example of the usage mode is shown in FIG. 2.

(S1: Acquire Clinical Data)

First, clinical data is acquired by applying medical practice such as examination, measurement, imaging, inquiry, or the like to a patient.

(S2: Store Clinical Data in Clinical DB)

The clinical data acquired in step S1 is stored into the clinical database 1100. Examination data or measurement data acquired by an examination apparatus or a measurement apparatus is sent to the electronic medical record system or the like via the intra-hospital network. Image data acquired by an imaging apparatus is sent to the image management system or the like via the intra-hospital network.

(S3: Start Creating Anonymized Data)

Creation of anonymized data is started in response to a predetermined trigger. Examples of the trigger include a preset schedule, an instruction issued by a doctor, or the like.

Here, a doctor or the like or a predetermined system/device (e.g., the clinical database 1100, the identifier conversion processor 1200, or the anonymization processor 1300) can select clinical data to be used for the creation of anonymized data, from the clinical data stored in the clinical database 1100.

(S4: Convert Internal ID to External ID)

The identifier conversion processor 1200 converts an internal identifier associated with the clinical data to be used for the creation of the anonymized data, to an external identifier.

(S5: Anonymize Confidential Data in Clinical Data)

The anonymization processor 1300 anonymizes predetermined confidential data included in the clinical data to be used for the creation of the anonymized data.

(S6: Store Anonymized Data Including External ID and Anonymized Clinical Data in Anonymized DB)

Anonymized data including the external identifier obtained in step S4 and the clinical data in which confidential data has been anonymized in step S5 is acquired. Anonymized data is created, for example, for individual external identifiers (that is, for individual patients). Anonymized data is stored in the anonymized database 1400.

(S7: Transmit Anonymized Data from Anonymized DB to Research Data Management System)

In response to a predetermined trigger, at least part of the anonymized data stored in the anonymized database 1400 is transmitted to the research data management system 2000.

(S8: Assign Research Project ID to Anonymized Data and Store Anonymized Data in Research DB)

The research data management system 2000 receives the anonymized data transmitted from the anonymized database 1400 in step S7.

The research data management system 2000 assigns a research project ID to the anonymized data. The research project ID is transmitted from the anonymized database 1400 along with the anonymized data, for example.

Alternatively, the research data management system 2000 may be configured to select a research project ID to be assigned to the anonymized data based on information indicating the transmission source of the anonymized data (e.g., a facility, the anonymized database 1400, a doctor, etc.) and correspondence information showing the correspondence between transmission sources and research project IDs.

The research data management system 2000 associates the research project ID and the anonymized data with each other and stores the research project ID and the anonymized data in the research database 2100. The research database 2100 manages anonymized data groups (that is, research data groups that can be used for research) for respective research project IDs.

(S9: User Requests Research Data)

A user requests the research data management system 2000 to provide data for research. The request includes a research user ID.

(S10: Select Research Data from Research DB)

The research data management system 2000 receives the request issued in step S9 and specifies a research data group corresponding to the research user ID included in the request. This process is executed by the research data provision processor 2200.

The research data provision processor 2200 includes correspondence information in which research data groups (that is, research project IDs) and research user IDs are associated with each other. By referring to the correspondence information, the research data provision processor 2200 can specify a research data group corresponding to the research user ID included in the request.

The research data provision processor 2200 can select research data to be provided, from among the research data group specified. For example, the research data provision processor 2200 can provide all the research data included in the research data group specified.

Alternatively, the research data provision processor 2200 can select research data that has not yet been provided to the user, from among the research data group specified. In this case, the research data provision processor 2200 can retain provision histories for respective users (e.g., for respective research user IDs), and can execute the selection of research data by referring to the provision history of the user.

Alternatively, levels may be set for respective pieces of research data, and levels of providable research data may be set for individual users (e.g., for each research user ID).

(S11: Format Conversion)

The research data provision processor 2200 converts the file format of the research data selected in step S10 into a file format corresponding to the user who sent the request in step S9.

For example, the research data provision processor 2200 includes correspondence information in which research user IDs and file formats are associated with each other. The research data provision processor 2200 can execute the specification of a file format with reference to the correspondence information. Alternatively, the request issued in step S9 may include file format information. As another alternative, the request issued in step S9 may include analysis type information, and a file format corresponding to the analysis type may be selected.

(S12: Provide Research Data to User)

The research data provision processor 2200 provides the research data whose file format has been converted in step S11, to the user who sent the request in step S9.

Modification Example

Modifications applicable to the exemplary embodiment will be described.

As in follow-up observations, clinical data of a single patient may be acquired more than once. The medical information processing system according to the exemplary embodiment may be configured to be capable of managing time series data of a single patient.

For example, the identifier conversion processor 1200 is configured to assign the same external identifier to the same internal identifier. With this, the same external identifier is assigned to the same patient.

It should be noted that clinical data of a single patient may be acquired in two or more different facilities. For example, clinical data of a patient who has visited a university hospital according to a referral from a clinic may sometimes include data acquired at the clinic and data acquired at the university hospital.

In a case where clinical data is acquired in two or more different facilities for a single patient, suppose that internal identifiers assigned at these facilities to the patient are the same. In this case, all identifier conversion processors 1200 installed in these facilities may be configured to convert this internal identifier to the same external identifier. Alternatively, the research data management system 2000 may be configured to be capable of associating two or more external identifiers converted at these facilities with one another. As a specific example, a predetermined code can be appended to each of the two or more external identifiers converted at these facilities.

In a case where clinical data is acquired in two or more different facilities for a single patient, suppose that internal identifiers assigned at these facilities to the patient are not the same. In this case, the medical information processing system is configured to be capable of associating two or more external identifiers converted at these facilities with one another.

In addition, as described above, items in the clinical data may include dates. The date may be acquisition date information representing the date on which the clinical data has been acquired. The anonymization processor 1300 does not anonymize the acquisition date information. That is, in the present example, the acquisition date information is not confidential data. With this, the anonymized data includes the acquisition date information on the corresponding clinical data.

Further, based on two or more pieces of acquisition date information included in two or more pieces of anonymized data corresponding to the same external identifier, the research database 2100 arranges and stores the two or more pieces of anonymized data according to a time series.

As a result, a plurality of pieces of clinical data acquired for a single patient to whom the same external identifier is assigned (or, for a single patient to whom two or more different external identifiers associated with one another are assigned) can be arranged in a time-dependent order according to pieces of acquisition date information.

Another example will be described in which clinical data is acquired in two or more different facilities for a single patient and internal identifiers assigned to the patient at these facilities are not the same. It is assumed that the two or more internal identifiers assigned to the patient are associated with one another.

For example, when two or more facilities have administrative relationship and/or capital relationship, it is possible to share a hospital information system between these facilities or link hospital information systems of these facilities. With this, two or more internal identifiers assigned to a single patient can be associated with one another.

By referring to such association, the identifier conversion processor 1200 can assign the same external identifier to the two or more different internal identifiers given to the patient at these facilities.

Also in the present example, the anonymized data includes acquisition date information indicating the date on which the clinical data has been acquired. Similarly, the research database 2100 is configured to arrange and store two or more pieces of anonymized data corresponding to the same external identifier according to a time-dependent order based on the two or more pieces of acquisition date information included in the two or more pieces of anonymized data.

Thus, even if different internal identifiers are given to the same patient, the same external identifier can be assigned to this patient, and therefore it becomes possible to manage a plurality of clinical data acquired for this patient according to a time-dependent order.

Second Embodiment

Figure 3:
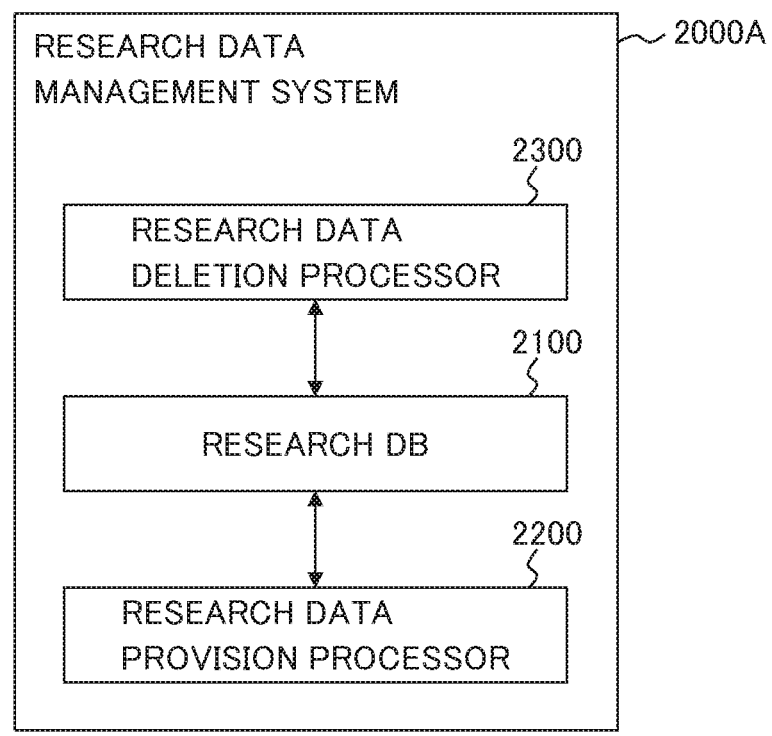
FIG. 3 is a schematic diagram illustrating an example of the configuration of the medical information processing system according to the exemplary embodiment.

It can be supposed that requests from patients or health facilities, law amendments, or the like causes the necessity of deleting research data once registered in the research database 2100. In consideration of such needs, the research data management system 2000A according to the exemplary embodiment shown in FIG. 3 includes the research data deletion processor 2300 in addition to the research database 2100 and the research data provision processor 2200 similar to those as in the first embodiment. Note that other elements of the present embodiment may be configured in the same manner as with those of the first embodiment.

The research data deletion processor 2300 receives a data deletion request from any of the first to the N-th facilities. The data deletion request includes an external identifier. A user who makes a data deletion request is, for example, a researcher (e.g., a doctor) who belongs to any of the first to the N-th facilities, any of the first to the N-th facilities, or an apparatus/device (e.g., a computer) installed in any of the first to the N-th facilities. The user identification and authentication are performed using passwords and identifiers (i.e., research user IDs) assigned in advance to users such as researchers, facilities, apparatuses/devices, and the like.

The research data deletion processor 2300 specifies research data corresponding to the external identifier included in the data deletion request. Since the research data (i.e., the anonymized data) includes the external identifier as described above, the research data deletion processor 2300 retrieves the research data including this external identifier from the research database 2100. Further, the research data deletion processor 2300 deletes the retrieved research data from the research database 2100.

Queries for searching research data are not limited to external identifiers. Other examples of the query include patient attributes, diseases, body parts, examination types, examination results, modality types, image analysis results, projects (e.g., research project IDs), and the like.

When the medical information processing system has the function according to the present embodiment, it becomes possible to appropriately perform additional registration of new patients, deletion of registered patients, edition of registered items, and the like. When the registration of a patient, the deletion, or the edition is performed, a patient list is updated. The patient list is managed, for example, by the research data management system 2000 (e.g., by the research data provision processor 2200). When the patient list is updated, the research data provision processor 2200 can inform related users of the updating.

It is also possible to manage patient lists in individual facilities. In this case, patients are identified using internal identifiers. When the registration of a patient, the deletion, or the edition is performed, the contents thereof are sent to the research data management system 2000. Regarding the data sent to the research data management system 2000, the patient is identified by the external identifier. When notified of changes in the patient list from a specific facility, the research data provision processor 2200 can inform related users of the notification. In addition, the research data provision processor 2200 can update the patient list managed by the research data provision processor 2200 itself.

Third Embodiment

A user can perform various types of analyses using the research data provided from the research data management system 2000. The research data management system 2000 may be configured to be able to manage analysis data obtained in a plurality of facilities in an integrated manner.

Figure 4:
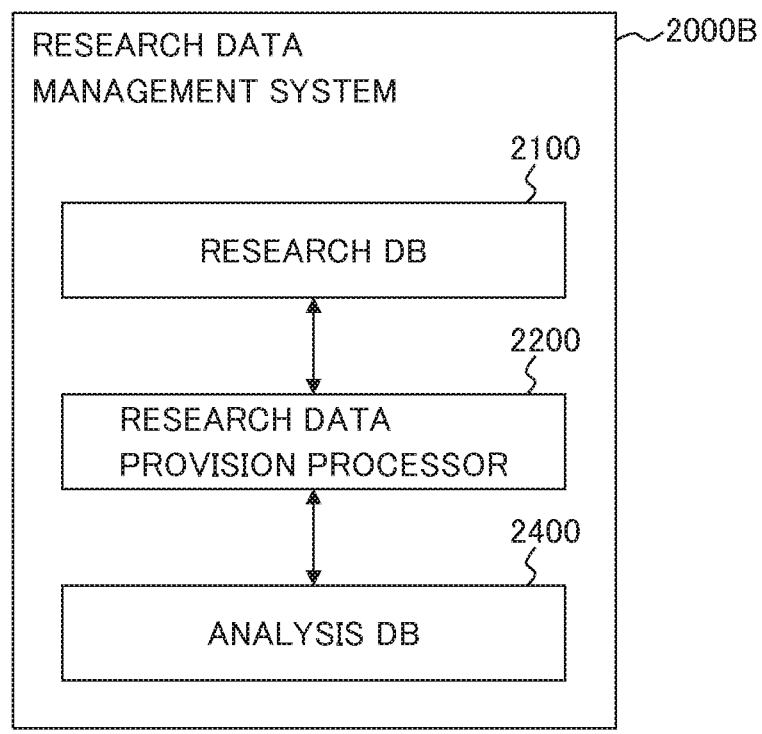
FIG. 4 is a schematic diagram illustrating an example of the configuration of the medical information processing system according to the exemplary embodiment.

In order to realize such an integrated management of analysis data, the research data management system 2000B according to the exemplary embodiment shown in FIG. 4 can be applied. The research data management system 2000B includes the analysis database 2400 in addition to the research database 2100 and the research data provision processor 2200 similar to those as in the first embodiment. Note that other elements of the present embodiment may be configured in the same manner as with those of the first embodiment.

The analysis database 2400 receives analysis data generated by a user through analysis based on the research data provided to the user from the research data management system 2000 and stores the analysis data. The analysis database 2400 manages analysis data for individual types of analyses, for example. The types of analyses include analysis methods, body parts, data used for analysis, patient attributes, and the like.

The research data management system 2000 can provide the analysis data stored in the analysis database 2400 to the first to the N-th facilities etc. For example, similar to the provision of research data, the research data provision processor 2200 may be configured to be able to provide analysis data in response to a request from the user.

Artificial intelligence technology may be applied to analysis of research data. Applications of artificial intelligence technology to the medical field include decision support, data analysis, data mining, transaction, image processing, image analysis, robots, gene analysis, and the like.

A medical artificial intelligence system is installed in, for example, health facilities, research institutions, etc., and is used by doctors and researchers. Other typical medical artificial intelligence systems may include servers and databases accessible from a plurality of health facilities and research institutions. A medical artificial intelligence system may be constructed using various types of computing technologies such as grid computing, cloud computing, parallel computing, distributed computing, and the like.

A medical artificial intelligence system carries out data mining, inference, statistical processing, machine learning, etc. based on databases, in which known information such as specialized books, dissertations and academic articles, medical information collected by health facilities etc. is stored, to acquire knowledge. The medical artificial intelligence system then stores the acquired knowledge in a database. By iteratively executing database updating and data mining and other processes, the accuracy and precision of the processing of the medical artificial intelligence system can be improved.

Note that the knowledge includes, for example, information that can be recognized and explicitly expressed, and includes at least either one of empirical knowledge (e.g., knowledge acquired through experience and learning) and theoretical knowledge (e.g., theoretical background knowledge and system of specialized information). Typical knowledge includes facts, rules, laws, judgment criteria, common sense, know-how, dictionaries, corpora, and the like. In addition, the knowledge may include information relating to processing executed by an artificial intelligence engine. For example, the knowledge may include weight parameters and bias parameters in a neural network. Medical knowledge and medical scientific knowledge (medical knowledge, taken together) are considered in the present embodiment.

A medical artificial intelligence system typically includes at least one computer and at least one storage device. The computer includes an artificial intelligence engine. The storage device is at least part of a database.

Fourth Embodiment

As described above, items anonymized by the anonymization processor 1300 (i.e., confidential items) are different depending on the region (a country, regional federation/coalition/union/association, etc.) where the medical information processing system is used. The present embodiment will describe the setting of confidential items. The medical information processing system according to the exemplary embodiment includes the elements shown in FIG. 5A provided in each facility and the research data management system 2000C shown in FIG. 5B.

Figure 5A:
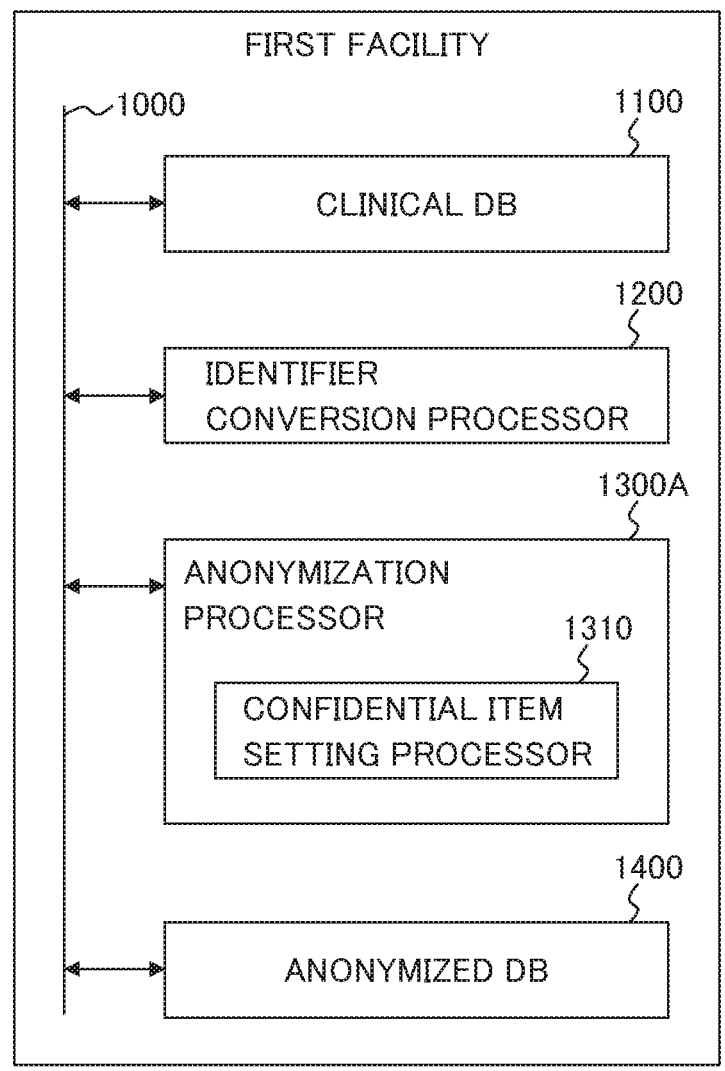
FIG. 5A is a schematic diagram illustrating an example of the configuration of the medical information processing system according to the exemplary embodiment.

As shown in FIG. 5A, the clinical database 1100, the identifier conversion processor 1200 and the anonymized database 1400 similar to those of the first embodiment are provided in the first facility (and in each of the second to the N-th facilities). Also, instead of the anonymization processor 1300 of the first embodiment, the anonymization processor 1300A is provided. The anonymization processor 1300A includes the confidential item setting processor 1310.

Figure 5B:
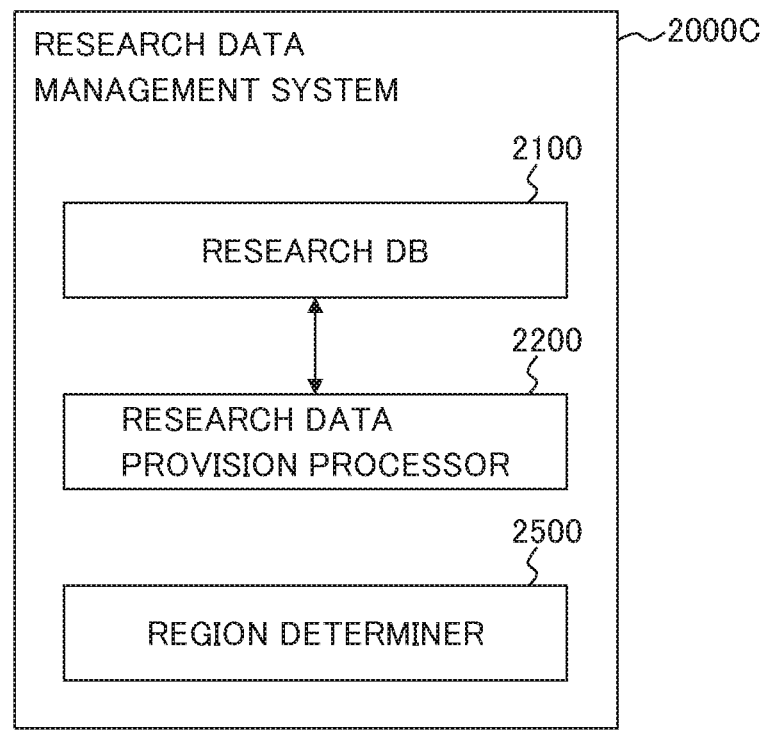
FIG. 5B is a schematic diagram illustrating an example of the configuration of the medical information processing system according to the exemplary embodiment.

The research data management system 2000C shown in FIG. 5B includes the region determiner 2500 in addition to the research database 2100 and the research data provision processor 2200 similar to those of the first embodiment. A region determiner need not be provided in the research data management system. For example, a region determiner may be provided in any of the first to the N-th facilities or may be provided in a location other than these.

The confidential item setting processor 1310 sets one or more confidential items. The anonymization processor 1300A anonymizes one or more pieces of data corresponding to the respective one or more confidential items set by the confidential item setting processor 1310 (i.e., one or more pieces of confidential data) among data included in clinical data used for creating anonymized data. The operation of setting confidential items is carried out manually or automatically.

The confidential item setting processor 1310 may be configured to set items according to the region where the facility exists. For example, the confidential item setting processor 1310 includes in advance two or more confidential item groups corresponding to respective two or more regions (e.g., confidential item list). Each of the confidential item groups is set, for example, based on the laws applied in its corresponding region. As an example, the confidential item setting processor 1310 includes in advance a confidential item group corresponding to the United States, a confidential item group corresponding to the European Union (EU), a confidential item group corresponding to Japan, a confidential item group corresponding to China, and the like. The confidential item setting processor 1310 receives input of region information that is information showing the region in which the facility exists. The operation of inputting the region information is carried out manually or automatically.

The medical information processing system according to the present embodiment may be configured to automatically determine the region where the facility exists. Such automatic determination is performed by the region determiner 2500.

For example, the region determiner 2500 can determine the region where the facility exists based on the Internet Protocol (IP) address corresponding to the facility. Alternatively, the region determiner 2500 can determine the region where the facility exists based on the location (address) of the facility, telephone number, fax number, electronic mail address, or the like. As another alternative, when a region determiner is provided inside the facility, the region determiner may be configured to utilize an arbitrary positioning system such as a satellite positioning system, a base station positioning system, or the like, to determine the position where the region determiner itself exists, thereby determining the region where the facility in which the region determiner is installed exists.

The determination result obtained by the region determiner 2500 (or another region determiner) is sent to the confidential item setting processor 1310. The confidential item setting processor 1310 can set one or more confidential items based on the determination result of the region input from the region determiner 2500 (or another region determiner).

<Actions>

Actions of a medical information processing system according to an exemplary embodiment will be described. Hereinafter, the actions will be described with reference to the first embodiment unless otherwise mentioned. Other embodiments and modifications thereof can also realize the same actions as those of the first embodiment, together with their unique actions.

Clinical data obtained by ordinary clinical medical practices (clinical practices) such as medical consultations and examinations is stored in the clinical database 1100.

In order to provide clinical data stored in the clinical database 1100 for joint research of a plurality of facilities, the identifier conversion processor 1200 converts a clinical patient ID (i.e., an internal identifier) to a research patient ID (i.e., an external identifier). This conversion can be interpreted as a mapping from clinical patient IDs to research patient IDs. The mapping may be either invertible or non-invertible. The identifier conversion processor 1200 can store the result of the mapping. The result of the mapping is the correspondence between clinical patient IDs and research patient IDs, which is sometimes referred to as an ID map or an ID mapping.

In addition, the anonymization processor 1300 acquires clinical data from the clinical database 1100 and anonymizes confidential data in the acquired clinical data to remove personal information from the clinical data. The anonymization does not directly apply processing to the clinical database 1100 (e.g., the electronic medical record system, the image management system, etc.), but processes clinical data extracted from the clinical database 1100.

In order for a plurality of facilities to share the clinical data from which personal information has been removed, the clinical data from which personal information has been removed is uploaded to the research data management system 2000 (the research database 2100 therein) where information security measures have been taken sufficiently, and then the clinical data from which personal information has been removed is stored and managed in a sharable mode. The research data management system 2000 includes a server on a cloud service, an intra-facility server of a research group, or the like that serves a function as the research data provision processor 2200.

The research database 2100 is an aggregation of clinical data uploaded from a plurality of facilities and constructs a large database. Such a large database is popularly known as big data. A sub-database is created in the research database 2100 for each research project. The sub-databases are identified using research project IDs.

A researcher can receive clinical data from a sub-database corresponding to the research project to which the researcher belongs. In this process, the research data provision processor 2200 can convert the file format of clinical data to a file format corresponding to the researcher or the research project and provide the format-converted clinical data to the researcher. For example, it is possible to provide clinical data converted to a file format suitable for data analysis tools familiar to the researcher.

In addition, analysis results derived by researchers can be stored in the analysis database 2400. For example, it is possible to acquire new knowledge by processing data stored in the analysis database 2400 using artificial intelligence technology or the like. In addition, it is possible to feed the acquired knowledge back into clinical settings (e.g., health facilities, medical locations). Doctors etc. can use the provided knowledge in everyday consultations and examinations. This establishes information circulation useful for both research and clinical practice. It is also possible to feed acquired knowledge back into research.

Since the medical information processing system is configured to manage clinical data using research patient IDs and research project IDs, clinical data of a specific patient can be appropriately deleted. For example, suppose that a specific patient is a subject of a plurality of research projects and the patient later expresses his/her wish to withdraw his/her offer to provide his/her clinical data to one specific research project out of the plurality of research projects. In this case, it is possible to specify the patient's clinical data provided to the specific research project using the research patient ID and the research project ID and then delete the specified clinical data. In this manner, the medical information processing system is capable of correctly performing deletion of clinical data for each patient, deletion of clinical data for each research project, and combinations of the deletion on a patient basis and that on a research project basis, as required.

The medical information processing system according to the exemplary embodiment can provide various kinds of graphical user interfaces (GUIs). Examples of GUIs include a tool for displaying patient data, a tool for displaying a patient list, a tool for selecting a patient, a tool for setting data items to be uploaded from a facility to the research data management system 2000 (referred to as the upload data item setting tool), and the like.

The upload data item setting tool includes, for example, a data item list representing a plurality of data items and a plurality of check boxes corresponding to the plurality of data items. An example of ophthalmologic application thereof includes "Patient Information", "Disease Information", "Treatment Information", and "Examination Information", and each of these includes a plurality of data items as follows.

Exemplary Patient Information includes "Age", "Height", "Weight, "Gender", "Smoker (or not)", "Blood pressure", and the like.

Exemplary Disease Information includes eye disease currently suffered (Current Ocular Disease), eye disease complication (Ocular Complication), diabetes mellitus (Diabetes), high blood pressure (Hypertension), history of eye disease in the past (Past Ocular History), and the like.

Exemplary Treatment Information includes a treatment type (Type) and the like.

Exemplary examination information includes intraocular pressure (IOP), subjective visual acuity (Subjective), objective refractive power (Objective), corneal curvature (Kerato), ocular axial length (Axial Length), tissue thickness in a macula of retina (Macular Thickness), thickness at the center of cornea (Central Corneal Thickness), Visual Field, raw images acquired using OCT (OCT raw images), parameters for OCT (OCT parameters), and the like.

The user inputs a check in the check box corresponding to a desired data item. The anonymization processor 1300 creates anonymized data including clinical data corresponding to the data item designated by the user.

The data item lists in the upload data item setting tool can be selectively applied according to the region where the facility exists. In addition, the anonymization processor 1300 compares the data item designated by the user and the default data items in accordance with the region where the facility exists. This makes it possible to determine whether the data item designated by the user is legitimate in the light of the laws of the region.

<Effects>

Effects of a medical information processing system according to an exemplary embodiment will be described.

The medical information processing system of an exemplary embodiment includes the followings: a plurality of clinical databases (1100) corresponding to a plurality of health facilities (first to N-th facilities); a plurality of identification conversion processors (1200) corresponding to a plurality of health facilities (first to N-th facilities); a plurality of anonymization processors (1300) corresponding to a plurality of health facilities (first to N-th facilities); a plurality of anonymization databases (1400) corresponding to a plurality of health facilities (first to N-th facilities); and a research data management system (2000) installed in a facility other than any of the plurality of health facilities (first to N-th facilities).

The clinical database (1100) stores clinical data acquired in a corresponding health facility in association with an internal identifier assigned to a patient.

The identifier conversion processor (1200) converts an internal identifier associated with clinical data stored in the clinical database (1100) of a corresponding health facility, to an external identifier.

The anonymization processor (1300) acquires clinical data from the clinical database (1100) of a corresponding health facility and anonymizes predetermined confidential data included in the clinical data acquired.

The anonymized database (1400) stores anonymized data including clinical data anonymized by the anonymization processor (1300) of a corresponding health facility and an external identifier associated with the anonymized clinical data by the identifier conversion processor (1200) of the corresponding health facility.

The research data management system (2000) includes a research database (2100) and a research data provision processor (2200).

The research database (2100) stores anonymized data provided from the plurality of anonymized databases (1400) corresponding to the plurality of health facilities for individual research projects that have been set in advance.

The research data provision processor (2200) receives a request from a user, reads out from the research database at least part of anonymized data associated with a research project to which the user belongs, and provides the read-out data to the user.

According to such an exemplary embodiment, the medical information processing system is configured to manage clinical data of individual patients using external identifiers instead of internal identifiers used in health facilities. Therefore, information security can be guaranteed.

In addition, the medical information processing system can automatically anonymize clinical data acquired in the plurality of health facilities, and automatically aggregate the anonymized clinical data in a research data management system installed in a facility other than any of the plurality of health facilities. Here, the research data management system is configured to manage the anonymized data (i.e., the research data) updated by the plurality of health facilities for individual research projects. Further, the research data management system can provide the research data to users on a research project basis.

Therefore, it is possible to realize a database of clinical data that can be effectively utilized from a plurality of facilities while securing security.

The medical information processing system of another exemplary embodiment is capable of performing data communication with a clinical database (1100) that stores clinical data acquired in a health facility in association with an internal identifier assigned to each patient. The medical information processing system includes the followings: a plurality of identification conversion processors (1200) corresponding to a plurality of health facilities (first to N-th facilities); a plurality of anonymization processors (1300) corresponding to a plurality of health facilities (first to N-th facilities); a plurality of anonymization databases (1400) corresponding to a plurality of health facilities (first to N-th facilities); and a research data management system (2000) installed in a facility other than any of the plurality of health facilities (first to N-th facilities).

The present exemplary embodiment does not include the clinical database (1100). Other aspects are the same as those in the above-described exemplary embodiment. Therefore, the present exemplary embodiment is also capable of realizing a database of clinical data that can be effectively utilized from a plurality of facilities while securing security.

In the medical information processing systems according to the exemplary embodiments, the research data management system (2000) may further include a research data deletion processor (2300). The research data deletion processor (2300) is configured to receive a data deletion request including an external identifier from one of the plurality of health facilities (the first to the N-th facilities), and to delete anonymized data including the external identifier included in the data deletion request from the research database (2100).

According to such a configuration, clinical data of a patient registered in the research database (2100) can be appropriately deleted after the registration as required.

In the medical information processing systems according to the exemplary embodiments, the anonymized data may include numerical data extracted from clinical data that has been anonymized by the anonymization processor (1300) and an external identifier that has been associated with the clinical data by the identifier conversion processor (1200).

According to such a configuration, anonymized data can be created by extracting numerical data such as examination data, measurement data, etc. from clinical data.

In the medical information processing systems according to the exemplary embodiments, the anonymized data may include image data extracted from clinical data that has been anonymized by the anonymization processor (1300) and an external identifier that has been associated with the clinical data by the identifier conversion processor (1200).

According to such a configuration, anonymized data can be created by extracting image data acquired by various kinds of medical imaging modalities from clinical data.

In the medical information processing systems according to the exemplary embodiments, at least one of the plurality of identifier conversion processors (1200) each may be configured to assign a same external identifier to a same internal identifier.

Further, the anonymized data may include acquisition date information that shows a date on which corresponding clinical data has been acquired.

In addition, the research database (2100) may be configured to store two or more pieces of anonymized data corresponding to a same external identifier according to a time-dependent order based on two or more pieces of acquisition date information included in the two or more pieces of anonymized data.

According to such a configuration, it is possible to manage a plurality of pieces of clinical data for a single patient according to a time-dependent order by using an external identifier. As a result, a user who receives research data can analyze the temporal change and variation in a plurality of pieces of clinical data for a single patient.

In the medical information processing systems according to the exemplary embodiments, the identifier conversion processor (1200) may be configured to assign a same external identifier to two or more different internal identifiers in a case where the two or more internal identifiers have been assigned to a single patient and the two or more internal identifiers are associated with one another.

Further, the anonymized data may include acquisition date information that shows a date on which corresponding clinical data has been acquired.

In addition, the research database (2100) may be configured to store two or more pieces of anonymized data corresponding to a single external identifier according to a time-dependent order based on two or more pieces of acquisition date information included in the two or more pieces of anonymized data.

According to such a configuration, in a case where two or more different internal identifiers have been assigned to a same patient and these internal identifiers are associated with one another, a same external identifier can be assigned to these internal identifiers. With this, it becomes possible to manage a plurality of pieces of clinical data for a single patient according to a time-dependent order, and a user who receives research data becomes able to analyze the temporal change and variation in the plurality of pieces of clinical data for a single patient.

In the medical information processing systems according to the exemplary embodiments, at least one of the plurality of health facilities each may include two or more medical locations (two or more facilities of the first to the N-th facilities). For example, any of the medical information processing systems according to the exemplary embodiments can be applied to a health facility having two or more medical locations (e.g., two or more facilities such as clinics and hospitals).

Further, the two or more internal identifiers may respectively correspond to the two or more medical locations.

According to such a configuration, when two or more different internal identifiers have been assigned to a single patient in two or more medical locations both belonging to a same health facility group, a same external identifier can be assigned to the two or more different internal identifiers. This makes it possible to manage a plurality of pieces of clinical data of a single patient according to a time-dependent order, and a user who receives research data becomes able to analyze the temporal change and variation in the clinical data of a single patient.

In the medical information processing systems according to the exemplary embodiments, in a case where at least one of the plurality of health facilities each includes two or more medical locations, it may be configured to assign a same internal identifier to a same patient in the two or more medical locations.

According to such a configuration, a same internal identifier (and therefore a same external identifier) can be assigned to a single patient in two or more medical locations all belonging to a same health facility group.

In the medical information processing systems according to the exemplary embodiments, upon receiving a request from a user, the research data provision processor (2200) reads out at least part of anonymized data (research data) associated with a research project to which the user belongs, from the research database (2100). Further, the research data provision processor (2200) converts a file format of the anonymized data read out from the research database (2100), to a file format associated in advance with the user or with the research project to which this user belongs. In addition, the research data provision processor (2200) provides the anonymized data whose file format has been converted, to the user.

According to such a configuration, research data whose file format has been automatically converted to a file format suitable for a user or a research project can be provided. Therefore, the user can perform analysis of the research data smoothly and promptly.

In the medical information processing systems according to the exemplary embodiments, the research data management system (2000) may include an analysis database (2400). The analysis database (2400) is configured to receive analysis data generated from an analysis carried out by a user based on provided anonymized data (research data), and to store the analysis data.

According to such a configuration, a database can be constructed by aggregating results of analyses carried out by users. Further, it is possible to process the aggregated results of analyses to acquire new knowledge, to feed the acquired knowledge back into clinical settings (e.g., health facilities, medical locations), and to feed the acquired knowledge back into research.

In the medical information processing systems according to the exemplary embodiments, at least one of the plurality of anonymization processors (1300) each may include a confidential item setting processor (1310). The confidential item setting processor (1310) is configured to set an item of the predetermined confidential data (a confidential item).

According to such a configuration, it is possible to arbitrarily and/or appropriately set a confidential item.

In the medical information processing systems according to the exemplary embodiments, the confidential item setting processor (1310) may be configured to set a confidential item according to a region in which a corresponding health facility is located.

According to such a configuration, a confidential item can be set according to the region (e.g., a country, regional federation/coalition/union/association, etc.) in which the health facility is located. More specifically, it is possible to set a confidential item in accordance with the laws or customs/traditions of the region.

The medical information processing systems according to the exemplary embodiments may further include a region determiner (2500). The region determiner (2500) determines a region in which the corresponding health facility is located. In addition, the confidential item setting processor (1310) may be configured to set a confidential item based on an output from the region determiner (2500).

According to such a configuration, it is possible to automatically determine a region in which a health facility is located and automatically set a confidential item according to the result obtained from the region determination.

A medical information processing method according to the exemplary embodiment includes the following plurality of processes.

In a clinical data storing process, a process of storing, into corresponding one of a plurality of clinical databases respectively associated with a plurality of health facilities, clinical data acquired in a corresponding health facility in association with an internal identifier assigned to a patient, is carried out.

In an identifier conversion process, a process of converting an internal identifier associated with clinical data stored in a clinical database of a corresponding health facility to an external identifier, is carried out by corresponding one of a plurality of identifier conversion processors respectively associated with the plurality of health facilities.

In an anonymization process, a process of acquiring clinical data from a clinical database of a corresponding health facility and a process of anonymizing predetermined confidential data included in the acquired clinical data, are carried out by corresponding one of a plurality of anonymization processors respectively associated with the plurality of health facilities.

In an anonymized data storing process, a process of storing, into corresponding one of a plurality of anonymized databases respectively associated with the plurality of health facilities, anonymized data including clinical data anonymized by an anonymization processor of a corresponding health facility and an external identifier associated with the anonymized clinical data by an identifier conversion processor of the corresponding health facility, is carried out.

In a research data storage process, a process of storing, into a research database installed in a facility other than any of the plurality of health facilities, anonymized data provided from the plurality of anonymized databases for individual research projects set in advance, is carried out.

In a research data provision process, a process of receiving a request from a user, a process of reading out from the research database at least part of anonymized data associated with a research project to which the user belongs, and a process of providing the at least part of anonymized data to the user, are carried out by a research data provision processor installed in a facility other than any of the plurality of health facilities.

According to such an exemplary embodiment, it is possible to realize a database of clinical data that can be effectively utilized from a plurality of facilities while securing security. It should be noted that any of the processes executable by the medical information processing systems according to the exemplary embodiments can be combined with the medical information processing method according to the exemplary embodiment.

It is possible to configure a computer program that makes a computer (or a group of computers) to execute the medical information processing method according to the exemplary embodiment. The computer program is configured to make a medical information processing system (e.g., a plurality of processors and a plurality of databases included in this medical information processing system) to execute the plurality of processes described above.

According to such a computer program, a database of clinical data that can be effectively utilized from a plurality of facilities can be realized while securing security.

A computer readable non-transitory recording medium in which the computer program according to the exemplary embodiment is recorded can be created. The non-transitory recording medium may be in any form, for example, a magnetic disk, an optical disk, a magneto-optical disk, a semiconductor memory, or the like.

It is possible to apply any of the various processes described as the medical information processing systems according to the exemplary embodiments, to the computer program according to the exemplary embodiment and/or the recording medium according to the exemplary embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions, additions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system comprising:
a plurality of clinical databases respectively associated with a plurality of health facilities, wherein each of the plurality of clinical databases stores clinical data acquired in a corresponding health facility in association with an internal identifier assigned to a patient;
a plurality of identifier conversion processors respectively associated with the plurality of health facilities, wherein each of the plurality of identifier conversion processors converts, as a non-invertible mapping, an internal identifier associated with clinical data stored in a clinical database of a corresponding health facility to an external identifier such that the internal identifier cannot be reproduced from the external identifier;
a plurality of anonymization processors respectively associated with the plurality of health facilities, wherein each of the plurality of anonymization processors acquires clinical data from a clinical database of a corresponding health facility and anonymizes predetermined confidential data included in the clinical data acquired;
a plurality of anonymized databases respectively associated with the plurality of health facilities, wherein each of the plurality of anonymized databases stores anonymized data including clinical data anonymized by an anonymization processor of a corresponding health facility and an external identifier associated with the anonymized clinical data by an identifier conversion processor of the corresponding health facility; and
a research data management system installed in a facility other than any of the plurality of health facilities, wherein the research data management system comprises:
a research database that stores anonymized data provided from the plurality of anonymized databases for individual research projects set in advance; and
a research data provision processor that receives a request from a user, reads out from the research database at least part of anonymized data associated with a research project to which the user belongs, and provides it to the user,
wherein, in a case where clinical data has been acquired in each of two or more different facilities for a single patient, two or more different internal identifiers have been assigned at the two or more different facilities to the single patient and the two or more internal identifiers are associated with each other, the identifier conversion processor assigns a same external identifier to the two or more internal identifiers, the anonymized data comprises acquisition date information that shows a date on which corresponding clinical data has been acquired, and the research database stores two or more pieces of anonymized data corresponding to a same external identifier according to a time-dependent order based on two or more pieces of acquisition date information included in the two or more pieces of anonymized data.

2. The medical information processing system of claim 1, wherein the research data management system further comprises a research data deletion processor that receives a data deletion request including an external identifier from one of the plurality of health facilities and deletes anonymized data including the external identifier included in the data deletion request from the research database.

3. The medical information processing system of claim 1, wherein the anonymized data comprises numerical data extracted from clinical data that has been anonymized by the anonymization processor and an external identifier that has been associated with the clinical data by the identifier conversion processor.

4. The medical information processing system of claim 1, wherein the anonymized data comprises image data extracted from clinical data that has been anonymized by the anonymization processor and an external identifier that has been associated with the clinical data by the identifier conversion processor.

5. The medical information processing system of claim 1, wherein
at least one of the plurality of identifier conversion processors each is configured to assign a same external identifier to a same internal identifier,
the anonymized data comprises acquisition date information that shows a date on which corresponding clinical data has been acquired, and
the research database stores two or more pieces of anonymized data corresponding to a same external identifier according to a time-dependent order based on two or more pieces of acquisition date information included in the two or more pieces of anonymized data.

6. The medical information processing system of claim 1, wherein in a case where at least one of the plurality of health facilities each comprises two or more medical locations, the two or more internal identifiers respectively correspond to the two or more medical locations.

7. The medical information processing system of claim 1, wherein in a case where at least one of the plurality of health facilities each comprises two or more medical locations, a same internal identifier is assigned to a same patient in the two or more medical locations.

8. The medical information processing system of claim 1, wherein the research data provision processor receives a request from a user, reads out at least part of anonymized data associated with a research project to which the user belongs from the research database, converts a file format of the read-out anonymized data to a file format associated in advance with the user or with the research project, and provides the converted anonymized data to the user.

9. The medical information processing system of claim 1, wherein the research data management system further comprises an analysis database that receives analysis data generated from an analysis performed by a user based on anonymized data provided to the user and stores the analysis data.

10. The medical information processing system of claim 1, wherein at least one of the plurality of anonymization processors each comprises a confidential item setting processor that sets an item of the predetermined confidential data.

11. The medical information processing system of claim 10, wherein the confidential item setting processor sets the item according to a region in which a corresponding health facility exists.

12. The medical information processing system of claim 11, further comprising a region determiner that determines a region in which the corresponding health facility exists,
wherein the confidential item setting processor sets the item based on an output from the region determiner.

13. A medical information processing system capable of performing data communication with a clinical database that stores clinical data acquired in a health facility in association with an internal identifier assigned to a patient, the medical information processing system comprising:
a plurality of identifier conversion processors respectively associated with a plurality of health facilities, wherein each of the plurality of identifier conversion processors converts, as a non-invertible mapping, an internal identifier associated with clinical data stored in a clinical database of a corresponding health facility to an external identifier such that the internal identifier cannot be reproduced from the external identifier;
a plurality of anonymization processors respectively associated with the plurality of health facilities, wherein each of the plurality of anonymization processors acquires clinical data from a clinical database of a corresponding health facility and anonymizes predetermined confidential data included in the clinical data acquired;
a plurality of anonymized databases respectively associated with the plurality of health facilities, wherein each of the plurality of anonymized databases stores anonymized data including clinical data anonymized by an anonymization processor of a corresponding health facility and an external identifier associated with the anonymized clinical data by an identifier conversion processor of the corresponding health facility; and
a research data management system installed in a facility other than any of the plurality of health facilities, wherein the research data management system comprises:
a research database that stores anonymized data provided from the plurality of anonymized databases for individual research projects set in advance; and
a research data provision processor that receives a request from a user, reads out from the research database at least part of anonymized data associated with a research project to which the user belongs, and provides it to the user,
wherein, in a case where clinical data has been acquired in each of two or more different facilities for a single patient, two or more different internal identifiers have been assigned at the two or more different facilities to the single patient and the two or more internal identifiers are associated with each other, the identifier conversion processor assigns a same external identifier to the two or more internal identifiers,
the anonymized data comprises acquisition date information that shows a date on which corresponding clinical data has been acquired, and
the research database stores two or more pieces of anonymized data corresponding to a same external identifier according to a time-dependent order based on two or more pieces of acquisition date information included in the two or more pieces of anonymized data.

14. The medical information processing system of claim 13, wherein the research data management system further comprises a research data deletion processor that receives a data deletion request including an external identifier from one of the plurality of health facilities and deletes anonymized data including the external identifier included in the data deletion request from the research database.

15. The medical information processing system of claim 13, wherein the anonymized data comprises numerical data extracted from clinical data that has been anonymized by the anonymization processor and an external identifier that has been associated with the clinical data by the identifier conversion processor.

16. The medical information processing system of claim 13, wherein the anonymized data comprises image data extracted from clinical data that has been anonymized by the anonymization processor and an external identifier that has been associated with the clinical data by the identifier conversion processor.

17. The medical information processing system of claim 13, wherein
at least one of the plurality of identifier conversion processors each is configured to assign a same external identifier to a same internal identifier,
the anonymized data comprises acquisition date information that shows a date on which corresponding clinical data has been acquired, and
the research database stores two or more pieces of anonymized data corresponding to a same external identifier according to a time-dependent order based on two or more pieces of acquisition date information included in the two or more pieces of anonymized data.

18. The medical information processing system of claim 13, wherein in a case where at least one of the plurality of health facilities each comprises two or more medical locations, the two or more internal identifiers respectively correspond to the two or more medical locations.

19. The medical information processing system of claim 13, wherein in a case where at least one of the plurality of health facilities each comprises two or more medical locations, a same internal identifier is assigned to a same patient in the two or more medical locations.

20. The medical information processing system of claim 13, wherein the research data provision processor receives a request from a user, reads out at least part of anonymized data associated with a research project to which the user belongs from the research database, converts a file format of the read-out anonymized data to a file format associated in advance with the user or with the research project, and provides the converted anonymized data to the user.

21. The medical information processing system of claim 13, wherein the research data management system further comprises an analysis database that receives analysis data generated from an analysis performed by a user based on anonymized data provided to the user and stores the analysis data.

22. The medical information processing system of claim 13, wherein at least one of the plurality of anonymization processors each comprises a confidential item setting processor that sets an item of the predetermined confidential data.

23. The medical information processing system of claim 13, wherein the confidential item setting processor sets the item according to a region in which a corresponding health facility exists.

24. The medical information processing system of claim 23, further comprising a region determiner that determines a region in which the corresponding health facility exists,
wherein the confidential item setting processor sets the item based on an output from the region determiner.

25. A method of processing medical information, the method comprising:
storing, in corresponding one of a plurality of clinical databases respectively associated with a plurality of health facilities, clinical data acquired in a corresponding health facility in association with an internal identifier assigned to a patient;
converting, as a non-invertible mapping, an internal identifier associated with clinical data stored in a clinical database of a corresponding health facility to an external identifier such that the internal identifier cannot be reproduced from the external identifier, by corresponding one of a plurality of identifier conversion processors respectively associated with the plurality of health facilities;
acquiring clinical data from a clinical database of a corresponding health facility and anonymizing predetermined confidential data included in the acquired clinical data, by corresponding one of a plurality of anonymization processors respectively associated with the plurality of health facilities;
storing, in corresponding one of a plurality of anonymized databases respectively associated with the plurality of health facilities, anonymized data including clinical data anonymized by an anonymization processor of a corresponding health facility and an external identifier associated with the anonymized clinical data by an identifier conversion processor of the corresponding health facility;
storing anonymized data provided from the plurality of anonymized databases for individual research projects set in advance, in a research database installed in a facility other than any of the plurality of health facilities; and
receiving a request from a user, reading out from the research database at least part of anonymized data associated with a research project to which the user belongs, and providing it to the user, by a research data provision processor installed in a facility other than any of the plurality of health facilities,
wherein, in a case where clinical data has been acquired in each of two or more different facilities for a single patient, two or more different internal identifiers have been assigned at the two or more different facilities to the single patient and the two or more internal identifiers are associated with each other, the identifier conversion processor assigns a same external identifier to the two or more internal identifiers,
the anonymized data comprises acquisition date information that shows a date on which corresponding clinical data has been acquired, and
the research database stores two or more pieces of anonymized data corresponding to a same external identifier according to a time-dependent order based on two or more pieces of acquisition date information included in the two or more pieces of anonymized data.

* * * * *